(12) United States Patent
Liu et al.

(10) Patent No.: US 9,919,978 B2
(45) Date of Patent: Mar. 20, 2018

(54) SELENIUM-DOPED NANO SILICA SOL USED FOR PRODUCING SELENIUM-ENRICHED RICE AND CAPABLE OF SUPPRESSING ABSORPTION AND ACCUMULATION OF HEAVY METALS IN PADDY RICE AND PREPARATION METHOD THEREFOR

(71) Applicant: GUANGDONG INSTITUTE OF ECO-ENVIRONMENTAL SCIENCE & TECHNOLOGY, Guangdong (CN)

(72) Inventors: Chuanping Liu, Guangdong (CN); Fangbai Li, Guangdong (CN); Jianghu Cui, Guangdong (CN); Xianghua Xu, Guangdong (CN)

(73) Assignee: Guangdong Institute of Eco-Environmental Science & Technology, Guangdong (CN)

( * ) Notice: Subject to any disclaimer, the term of this patent is extended or adjusted under 35 U.S.C. 154(b) by 0 days.

(21) Appl. No.: 14/771,189

(22) PCT Filed: Oct. 10, 2014

(86) PCT No.: PCT/CN2014/088288
§ 371 (c)(1),
(2) Date: Aug. 27, 2015

(87) PCT Pub. No.: WO2015/096533
PCT Pub. Date: Jul. 2, 2015

(65) Prior Publication Data
US 2016/0289129 A1    Oct. 6, 2016

(30) Foreign Application Priority Data

Dec. 26, 2013  (CN) .......................... 201310737996

(51) Int. Cl.
*A01N 59/02*   (2006.01)
*C05D 9/02*    (2006.01)

(52) U.S. Cl.
CPC ............... *C05D 9/02* (2013.01); *A01N 59/02* (2013.01)

(58) Field of Classification Search
CPC ...................................................... C05D 9/02
See application file for complete search history.

(56) References Cited

U.S. PATENT DOCUMENTS

| 7,585,898 B2 * | 9/2009 | Thothathri | ............... | C12N 1/12 |
| | | | | 435/257.1 |
| 8,695,275 B2 * | 4/2014 | Havrda | .................... | C05D 9/00 |
| | | | | 47/59 S |

(Continued)

FOREIGN PATENT DOCUMENTS

| CN | 100469249 C | 3/2009 |
| CN | 101830735 B | 5/2012 |
| CN | 101851133 B | 2/2013 |

*Primary Examiner* — Wayne Langel
(74) *Attorney, Agent, or Firm* — Hahn Loeser & Parks, LLP—San Diego (57) ABSTRACT

The present invention discloses a selenium-doped nano-silica sol capable of both inhibiting the absorption and accumulation of heavy metal in rice and producing a selenium-rich rice, and a preparation method thereof. The selenium-doped nano-silica sol of the present invention is prepared mainly by using a nano-silica sol as a carrier, sodium selenite and the like as a raw material, vitamin C and the like as a reducing agent, and polyvinylpyrrolidone and the like as an emulsifier, and doping and dispersing selenium in a specific ratio in a silica sol so as to form a selenium-doped nano-silica sol with a special structure and function. The selenium-doped nano-silica sol prepared according to the invention has high stability and high concentration, and is uniform and transparent, and has a silica content of up to (Continued)

20% or more, a selenium content of up to 1% or more, and low impurity content. The selenium-doped nano-silica sol of the present invention has a pH close to neutral, wherein selenium, in a nano particle form, is dispersed in colloidal silica, with a particle size of less than 50 nm; and after the foliar application, it can significantly promote the growth of crops, inhibit the absorption and accumulation of arsenic and cadmium in crops, and increase the selenium content in crops, and has no toxic and side effects on crops, and is safe to application.

8 Claims, 5 Drawing Sheets

(56) References Cited

U.S. PATENT DOCUMENTS

| | | | |
|---|---|---|---|
| 9,017,444 B2* | 4/2015 | Liu | C05D 9/00 71/62 |
| 2004/0091417 A1* | 5/2004 | Yadav | B82Y 30/00 423/592.1 |
| 2011/0064798 A1* | 3/2011 | Suvee | A61K 8/044 424/451 |
| 2012/0276165 A1* | 11/2012 | Laane | A01N 59/00 424/400 |

* cited by examiner

SELENIUM-DOPED NANO SILICA SOL USED FOR PRODUCING SELENIUM-ENRICHED RICE AND CAPABLE OF SUPPRESSING ABSORPTION AND ACCUMULATION OF HEAVY METALS IN PADDY RICE AND PREPARATION METHOD THEREFOR

CROSS-REFERENCE TO RELATED APPLICATIONS

The present application is a U.S. National Stage entry under 35 U.S.C. § 371 of International Application No. PCT/CN2014/088288 filed on Oct. 10, 2014, designating the United States of America and published in Chinese on Jul. 2, 2015, which in turn claims priority to Chinese Patent Application No. 201310737996.X filed on Dec. 26, 2013, each of which is hereby incorporated by reference in its entirety.

TECHNICAL FIELD

The invention belongs to the field of soil and fertilizer, in particular to a selenium-doped nano-silica sol capable of both inhibiting the absorption and accumulation of heavy metal in rice and producing a selenium-rich rice and a preparation method thereof.

BACKGROUND ART

Selenium is an essential trace element in animals and humans, is a component of glutathione peroxidase, and has an antioxidative effect. In 1973, World Health Organization (WHO) announced that selenium was an essential nutrient element in humans; and in 1988, Chinese Nutrition Society classified selenium as an essential nutrient element in humans. Selenium has a variety of physiological functions in humans and animals, for example selenium has anti-cancer, anti-tumor and anti-aging effects, etc. Many endemic diseases in China, such as Keshan disease, Kashin-Beck disease, etc., all have close relationships with the selenium deficiency in the environment. Therefore, selenium plays an important role on human health.

The selenium required in human body must be acquired from the diet, International Selenium Society recommends the daily intake of selenium in human body of 60-400 µg, and Chinese Nutrition Society recommends the daily intake of selenium in human body of 50-200 µg. However, the survey from Chinese Nutrition Society has showed that the average daily intake of selenium in Chinese residents is only 26-32 µg; there are up to 22 selenium deficiency provinces in China, and the selenium deficiency area accounts for about 72% of the land area of China. Although food additives, healthcare products or drugs can be used to quickly replenish the selenium deficiency in human body, but such selenium replenishment method has a high cost, small coverage area, and can not fundamentally solve the effective replenishment of the selenium nutrition in human body in a large selenium deficiency area. Increasing the selenium content in agricultural products is a fundamental way to prevent the selenium deficiency diseases in human from the source. As rice is a main food crop in China, increasing the selenium content in rice, and producing a selenium-rich rice has an important significance to human selenium nutrition and health.

Also it was reported that selenium can reduce the absorption and accumulation of heavy metals, such as arsenic, lead, cadmium, chromium and other elements in rice; and improve the heavy metal resistance of rice. As the heavy metal pollution in soil is one of the most important and the most serious pollution issues in soil, it has been widely concerned and attended in the world. Heavy metal pollution in soil in China is also very prominent, about one sixth of the prime farmlands are subjected to varying degrees of heavy metal pollution; in China, only the farmland contaminated by Cd is up to 12,000 hectares. It is estimated that the food contaminated by heavy metal is up to 12,000 thousand tons per year in China, resulting in a direct economic loss of more than 20 billion CNY. And the quality and safety issues of agricultural products and the mass events caused by soil pollution are increasing every year, which has become an important factor for affecting the public health and social stability. At present, the methods for repairing the heavy metal pollution in soil in China and other countries comprise physical remediation, chemical remediation, bioremediation methods and the like. Physical and chemical remediation methods are suitable for a local site with a small pollution range and a serious pollution degree, and often have a large engineering quantity and high cost, and often lead to the destruction of the soil structure and the leaching loss of some nutritional elements. Bioremediation method, especially phytoremediation technology, is a currently preferred method, and it has become a currently research hotspot and frontier in China and other countries due to the advantages of friendly to environment, low cost, and non-secondary pollution, etc. However, as the phytoremediation technology is not adapted to high concentration pollution and combined pollution, the reparing plant is not suitable for the soil characteristics, climate, etc., in the contaminated sites, such technology is not completely adaptive to the harnessing of the heavy metal pollution in farmland, and at present it has not reached the level of practical application, the phytoremediation technology is still hard to get a commercial application now. However, from the viewpoint of the nutritional and physiological regulation of agricultural crops, it has provide a new idea for addressing the ecological security issue in the regional farmland by improving the heavy metal resistance in agricultural crops, and inhibiting the absorption and accumulation of heavy metal in agricultural crops.

Improving the heavy metal resistance of rice by increasing the selenium nutrition in rice, not only can reduce the absorption and accumulation of heavy metal in rice, but also can increase the selenium-enriched level in rice. Therefore, it has attracted a widespread concern for the development and application of a selenium-rich fertilizer. The selenium-rich fertilizers in China and other countries mainly comprise water-soluble foliage selenium-rich fertilizers, inorganic and organic selenium-rich compound fertilizers, selenium-rich slow-release fertilizers, etc. Although at present there are lots of patents for the preparation of the selenium-rich fertilizers, most of them disclose that the selenium-rich fertilizers are prepared by simply mixing the inorganic selenite salt with the livestock and poultry feces or the agricultural wastes or by microbial fermentation. The fertilizers prepared using these methods have a low selenium content, often less than 0.1%, and the inorganic selenite salt itself has a biological toxicity, the excessive application amount will make damage to crops, and the safety to application is poor. It has not been reported about a process for preparing a high active, safe and efficient selenium-rich foliage silicon fertilizer by using a nano-silica sol as a carrier. Silicon is a special beneficial element, and the regulation of silicon nutrition in rice can both improve the heavy metal resistance of crops, and inhibit the absorption of heavy metal in crops. Our previous patents "Rare Earth Compound Silicon Sol Capable of Inhibiting Heavy Metal Absorption of Rice (ZL200610036994.8)", "Composite Foliage Silicon Fertilizer for Lowering Contents of Heavy Metal and Nitrate in Vegetable and Preparation Method Thereof (ZL 201010156359.X)" and "Preparation and Using Method of Foliage Silicon Fertilizer (ZL201010156358.5)" disclosed a foliage silicon fertilizer or a foliage silicon fertilizer doped with trace element, or a foliage silicon fertilizer doped with rare earth element, respectively. Currently there are no selenium-doped foliage silicon fertilizer products disclosed in China. As selenium has a special physiological function, and can improve the heavy metal resistance in crops, when the selenium-doped foliage silicon fertilizer is prepared, it will inevitably improve the silicon fertilizer product in inhibiting the heavy metal absorption capacity in crops, and at the same time can produce a selenium-rich agricultural product; which not only meets the needs for producing a selenium-rich agricultural product, but also provides a new way for the harnessing of the soil heavy metals in farmland in China.

SUMMARY OF THE INVENTION

The object of the present invention is to provide a safe and efficient selenium-doped nano-silica sol capable of both inhibiting the absorption and accumulation of heavy metal in rice and producing a selenium-rich rice, which not only can inhibit the absorption and accumulation of heavy metal in rice, but also can produce a selenium-rich rice, and a preparation method thereof, the preparation process is simple, the production cost is low, the prepared selenium-doped nano-silica sol product capable of both inhibiting the absorption and accumulation of heavy metal in rice and producing a selenium-rich rice has a stable performance, with a particle size of less than 50 nm and homogenous distribution, the product is an uniform and transparent sol, with a pH close to neutral, and can be widely applied in the aspects such as inhibiting the absorption and accumulation of heavy metal in crops, and at the same time producing a selenium-rich rice.

The selenium-doped nano-silica sol capable of both inhibiting the absorption and accumulation of heavy metal in rice and producing a selenium-rich rice disclosed in the present invention is prepared mainly by using a nano-silica sol as a carrier, sodium selenite and the like as a raw material, vitamin C and the like as a reducing agent, and polyvinylpyrrolidone and the like as an emulsifier, and doping and dispersing selenium in a specific ratio in a silica sol so as to form a selenium-doped nano-silica sol capable of both inhibiting the absorption and accumulation of heavy metal in rice and producing a selenium-rich rice, with a special structure and function.

The selenium-doped nano-silica sol capable of both inhibiting the absorption and accumulation of heavy metal in rice and producing a selenium-rich rice disclosed in the present invention is prepared by the following method, which comprises the steps of:

(1) preparation of a metal silicate solution: a metallic silicon powder or a metal silicate is added with stirring to an alkaline solution with a concentration of 0.1~5 M, so as to prepare a metal silicate solution, wherein the concentration of the metallic silicon powder or the metal silicate is 5% by weight to saturation, pH 10~13; wherein the metal silicate is $Na_2SiO_3$, $K_2SiO_3$ or $Li_2SiO_3$;

(2) preparation of an acidic silica sol precursor: the metal silicate solution is subjected to a cation exchange treatment, the collected solution is controlled at a pH of 1~4, the collected solution is heated to 35-90° C., then carried out standing, cooling and aging, so as to obtain an acidic silica sol precursor;

(3) preparation of an acidic selenium-doped solution: a selenium-containing compound is dissolved in a dilute acid solution with stirring, so as to prepare an acidic selenium-doped solution with a selenium content of 0.1 to 10% by mass, and the acidic selenium-doped solution is controlled at a pH of 1~4; wherein the selenium-containing compound is seleninic acid, sodium selenite, potassium selenite, or sodium hydroxide selenite;

(4) preparation of a selenium-doped emulsion: an emulsifier is added with stirring to the acidic selenium-doped solution in step (3), the final mass percentage of the emulsifier is controlled at 0.05~5%, so as to obtain a selenium-doped emulsion; wherein the emulsifier is polyvinylpyrrolidone (PVP), polyvinyl alcohol (PVA), Tween or Span series;

(5) preparation of a selenium-doped acidic silica sol precursor: the selenium-doped emulsion in step (4) is added with stirring to the acidic silica sol precursor in step (2) so as to obtain a selenium-doped acidic silica sol precursor, wherein the selenium-doped acidic silica sol precursor has a mass percentage ratio between silicon and selenium of 3~200:1;

(6) the selenium-doped acidic silica sol precursor in step (5) is added to an alkaline solution formulated with a basic catalyst at 30° C.~90° C., and the addition is not stopped until the alkaline solution arrives at a pH of 7~9, stirring and reaction are continued for 30~90 min, so as to obtain a selenium-doped silica sol precursor; wherein the basic catalyst is sodium hydroxide, potassium hydroxide, urea, aqueous ammonia, or sodium silicate solution;

(7) the selenium-doped silica sol precursor in step (6) is added to a reducing agent solution at 30° C.~90° C., until the pale red color of the sol is no longer deepened, after selenium is sufficiently reduced, the sol is continued to stir and react for 2 hours or more time, then dialyzed twice or more times, so as to obtain a selenium-doped nano-silica sol capable of both inhibiting the absorption and accumulation of heavy metal in rice and producing a selenium-rich rice; wherein the reducing agent is ascorbic acid (Vc), glutathione or reducing sugars.

The alkaline solution in step (1) is formulated with sodium hydroxide, potassium hydroxide or aqueous ammonia, preferably with a concentration of 0.1~2 M.

The collected solution in step (2) preferably has a pH of 2~3.5, and preferably the collected solution is heated to 45-55° C.

The dilute acid solution in step (3) can be hydrochloric acid, nitric acid, sulfuric acid, phosphoric acid, etc., preferably hydrochloric acid; the selenium content in the acidic selenium-doped solution is preferably 2~7.6% by mass; the acidic selenium-doped solution is preferably controlled at a pH of 1~2.

The emulsifier in step (4) is preferably Tween, and the final mass percentage of the emulsifier is preferably controlled at 0.5~2%.

The selenium-doped acidic silica sol precursor in step (5) preferably has a mass percentage ratio between silicon and selenium of 9~20:1.

The alkaline solution formulated with a basic catalyst in step (6) is preferably controlled at a temperature of 45° C.~85° C., and the stirring and reaction is continued for 30~60 min.

The reducing agent in step (7) is preferably ascorbic acid (Vc), and the solution is preferably controlled at a temperature of 50° C.~85° C.

The selenium-doped nano-silica sol capable of both inhibiting the absorption and accumulation of heavy metal in rice and producing a selenium-rich rice prepared according to the present invention has high stability and high concentration, and is uniform and transparent, and as compared with the prior art, it has the following advantages:

1. The selenium-doped nano-silica sol prepared by the methods of the present invention has a silica content of up to 20% or more, a selenium content of up to 1% or more, and low impurity content.

2. The selenium-doped nano-silica sol of the present invention has a pH close to neutral, wherein selenium, in a nanoparticle form, is dispersed in colloidal silica, with a colloidal particle size of less than 50 nm; after foliar application, it can significantly promote the crop growth, inhibit the absorption and accumulation of arsenic in crops, and increase the selenium content in crops and has no toxic and side effects on crops, and is safe to application.

3. The preparation method of the present invention is carried out at a low temperature and under atmospheric pressure, with a mild condition, simple process, and easy to operation, so that it is easy to carry out a large-scale production. In addition, it has a wide source of the raw material, low cost, and high yield, which facilitate its promotion.

DETAILED DESCRIPTION OF THE INVENTION

The following examples are provided to further illustrate the present invention, and not intended to make any limitation.

Example 1

Preparation of a selenium-doped nano-silica sol capable of both inhibiting the absorption and accumulation of heavy metal in rice and producing a selenium-rich rice.

Figure 1:
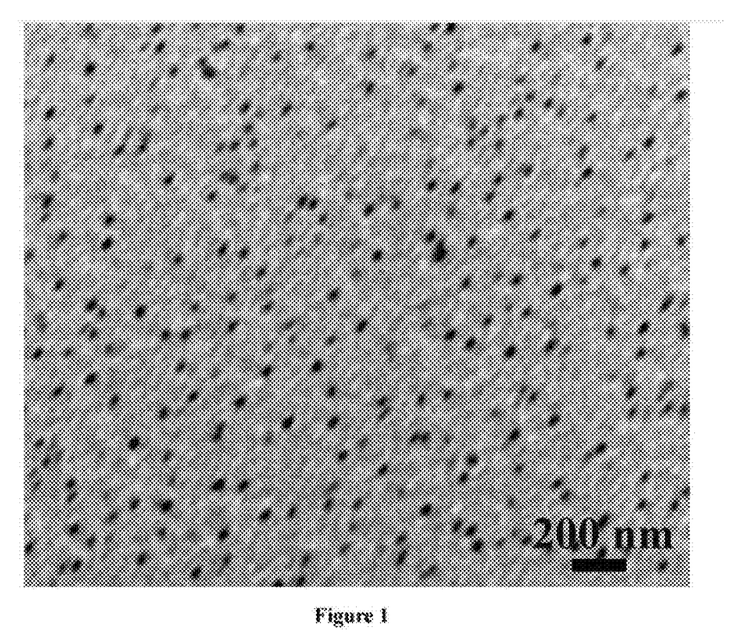
FIG. 1 shows a scanning electron micrograph of the selenium-doped silica sol with 1% selenium in example 1.
Figure 2:
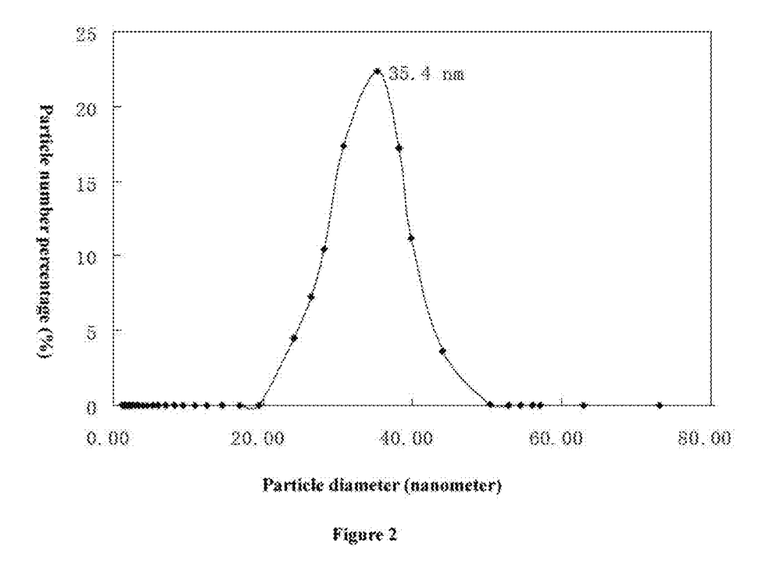
FIG. 2 shows a particle size distribution of the selenium-doped silica sol with 1% selenium in example 1.

200 mL of water was metered, 1 g sodium hydroxide was added, a stirrer was actuated, and the temperature was heated to 55° C., then 250 g $Na_2SiO_3$ was added, after sufficiently dissolved, the temperature was cooled to the room temperature, so as to obtain a metal silicate solution with a pH of 12.8, wherein the mass percentage of the metal silicate was 55.5%. The above-mentioned metal silicate solution was passed through a 100 mL (wet volume) of hydrogen-type strong acidic cation exchange resin multi-stage column in an uniform speed of 5 mL/min, the collected solution at the outlet of the column was controlled at a pH between 2~3, the collected solution was heated to 50° C. with stirring by microwave (or water bath), then carried out standing, cooling, and aging for 30 min, so as to obtain an acidic silica sol precursor, ready for use. 0.5, 2.5, 5, 10 g of sodium selenite were weighed respectively, dissolved in 50 mL 0.01 M dilute hydrochloric acid, so as to prepare an acidic selenium-doped solution, with a pH of 2; a stirrer was actuated and the acidic selenium-doped solution was heated to a temperature of 55° C., then 1 g Tween 20 was slowly added to the acidic selenium-doped solution; stirring was continued for about 1 hour, so as to obtain a selenium-doped emulsion. The above-mentioned selenium-doped emulsion was added dropwise into the-abovementioned selenium-doped acidic silica sol precursor, the addition was carried out with stirring, and the temperature was maintained at 55° C.; after the dropwise addition was complete, stirring was continued for 30 min, so as to obtain a selenium-doped acidic silica sol precursor. The selenium-doped acidic silica sol precursor was then slowly added to 20 ml aqueous ammonia with a concentration of 25-28%, the addition was carried out with stirring, and the temperature was maintained at 45° C., after the dropwise addition was complete, the pH value arrived at 7~9, stirring and reaction were continued at 45° C. for 30 min, so as to prepare a selenium-doped silica sol precursor. The selenium-doped silica sol precursor solution was slowly added to 50 mL 0.1 M ascorbic acid (Vc) which was heated to 50° C. with stirring by microwave (or water bath), the addition was carried out dropwise, until the pale red color of the sol was no longer deepened, after selenium was sufficiently reduced, stirring was continued for 2 hours or more time, so as to obtain a sol; the prepared sol was dialyzed two times, and concentrated to 200 mL by evaporation so as to obtain an uniform, stable and translucent high purity selenium-doped nano-silica sol, i.e., the selenium-doped nano-silica sol capable of both inhibiting the absorption and accumulation of heavy metal in rice and producing a selenium-rich rice in the present example. The obtained high purity selenium-doped nano-silica sol had a silica content of 20%, selenium contents of 0.1%, 0.5%, 1% and 2% respectively. FIG. 1 showed a scanning electron micrograph of the selenium-doped nano-silica sol with a selenium content of 1%, and FIG. 2 showed a particle size distribution of the selenium-doped nano-silica sol with a selenium content of 1%.

Example 2

Preparation of a selenium-doped nano-silica sol capable of both inhibiting the absorption and accumulation of heavy metal in rice and producing a selenium-rich rice.

200 mL of water were metered, 20 g potassium hydroxide was added, a stirrer was actuated and the temperature was heated to 85° C., then 15 g metallic silicon powder was added, after sufficiently dissolved, the temperature was cooled to the room temperature, so as to prepare a metal silicate solution with a pH of 13, wherein the mass percentage of the metallic silicon was 6.4%. The above-mentioned metal silicate solution was passed through a 100 mL (wet volume) of hydrogen-type strong acidic cation exchange resin multistage column in an uniform speed of 5 mL/min, the collected solution at the outlet of the column was controlled at a pH value between 2.5~3.5, the collected solution was heated to 90° C. with stirring by microwave (or water bath), carried out standing, cooling, and aging for 30 min, so as to obtain an acidic silica sol precursor, ready for use. 0.6, 3, 8, 12 g potassium selenite were weighed respectively, dissolved in 50 mL 0.1 M of dilute nitric acid, so as to prepare an acidic selenium-doped solution, with a pH of 1.2; a stirrer was actuated and the acidic selenium-doped solution was heated to 85° C., then 2.5 g polyvinylpyrrolidone (PVP) was slowly added to the acidic selenium-doped solution; stirring was continued for about 1 hour, so as to obtain a selenium-doped emulsion. The above-mentioned selenium-doped emulsion was added dropwise to the above-mentioned selenium-doped acidic silica sol precursor, the addition was carried out with stirring, and the temperature was maintained at 85° C.; after the addition was complete, stirring was continued for 90 min, so as to obtain a selenium-doped acidic silica sol precursor. The selenium-doped acidic silica sol precursor was then slowly added to 20 ml sodium hydroxide solution with a concentration of 0.5-1.2 M, the addition was carried out with stirring, and the temperature was maintained at 85° C., after the dropwise addition was complete, the pH value arrived at 7~9, stirring and reaction were continued at 85° C. for 30 min, so as to prepare a selenium-doped silica sol precursor. The selenium-doped silica sol precursor solution was slowly added to 50 mL 0.5 M glutathione solution which was heated to 85° C. with stirring by microwave (or water bath), the addition was carried out dropwise until the pale red color of the sol was no longer deepened, after selenium was sufficiently reduced, stirring was continued for 2 hours or more time, so as to obtain a sol; the prepared sol was dialyzed twice, and concentrated to 200 mL by evaporation, so as to obtain an uniform, stable and translucent high purity selenium-doped nano-silica sol, i.e., the selenium-doped nano-silica sol capable of both inhibiting the absorption and accumulation of heavy metal in rice and producing a selenium-rich rice in the present example. The obtained high purity selenium-doped nano-silica sol had a silica content of 15%, and selenium contents of 0.12%, 0.58%, 1.5% and 2.3% respectively.

Example 3

Preparation of a selenium-doped nano-silica sol capable of both inhibiting the absorption and accumulation of heavy metal in rice and producing a selenium-rich rice.

200 mL 5% by mass of dilute aqueous ammonia was metered, a stirrer was actuated and the temperature was heated to 35° C., then 50 g $K_2SiO_3$ was added, after sufficiently dissolved, the temperature was cooled to the room temperature, so as to prepare a metal silicate solution with a pH of 10.5, wherein the mass percentage of the metal silicate was 20%. The above-mentioned metal silicate solution was passed through a 100 mL (wet volume) of hydrogen-type strong acidic cation exchange resin multi-stage column in an uniform speed of 5 mL/min, the collected solution at the outlet of the column was controlled at a pH value between 2.5~3.5, the collected solution was heated to 35° C. with stirring by microwave (or water bath), carried out standing, cooling, and aging for 30 min, so as to obtain an acidic silica sol precursor, ready for use. 0.5, 1, 2, 4 g sodium hydrogen selenite were weighed respectively, dissolved in 50 mL 0.01 M dilute sulfuric acid, so as to prepare an acidic selenium-doped solution, with a pH of 1.8; a stirrer was actuated and the acidic selenium-doped solution was heated to 35° C., 0.25 g Span 60 was then slowly added into the acidic selenium-doped solution; stirring was continued for about 1 hour, so as to prepare a selenium-doped emulsion. The above-mentioned selenium-doped emulsion was added dropwise to the above-mentioned selenium-dope acidic silica sol precursor, the addition was carried out with stirring, and the temperature was maintained at 35° C.; after the addition was complete, stirring was continued for 30 min, so as to obtain a selenium-doped acidic silica sol precursor. The selenium-doped acidic silica sol precursor was then slowly added to 20 ml potassium hydroxide solution with a concentration of 0.1-0.5 M, the addition was carried out with stirring, and the temperature was maintained at 35° C., after the dropwise addition was complete, the PH value arrived at 7~9, stirring and reaction were continued at 35° C. for 60 min, so as to prepare a selenium-doped silica sol precursor. The selenium-doped silica sol precursor solution was slowly added to 50 mL 0.1 M glucose solution which was heated to 35° C. with stirring by microwave (or water bath), the addition was carried out dropwise until the pale red color of the sol was no longer deepened, after selenium was sufficiently reduced, stirring was continued for 2 hours or more, so as to obtain a sol; the prepared sol was dialyzed twice, and concentrated to 200 mL by evaporation, so as to obtain an uniform, stable and translucent high purity selenium-doped nano-silica sol, i.e., the selenium-doped nano-silica sol capable of both inhibiting the absorption and accumulation of heavy metal in rice and producing a selenium-rich rice in the present example. The prepared high purity selenium-doped nano-silica sol had a silica content of 10%, and selenium contents of 0.1%, 0.2%, 0.4% and 0.8% respectively.

Example 4

The pot experiment for showing the effects of relieving the heavy metal poison in rice by foliar application of the selenium-doped nano-silica sol.

The soils to be tested were collected from an arsenic-contaminated rice field, in Yanhong Town, Chenghai District, Shantou City, Guangdong Province, China, the surface layer of the cultivated soils (0-10 cm) in the rice field was taken as the soil, air-dried and sieved, 10 kg of the soil were weighed and filled into barrels, wherein the basic physical and chemical properties of the soil were as follows: pH 6.12, organic matter 2.73%, total nitrogen 1.5 g/kg, total phosphorus 1.02 g/kg, total potassium 11.3 g/kg, CEC 8.75 cmol/kg, total arsenic 93.6 mg/kg, and total selenium 0.879 mg/kg.

Cultivation and treatment of rice: the rice variety was Youyou 128, the rice seed surface was disinfected for 15 minutes with 5% sodium hypochlorite solution, after washing with tap water, germination and seedling were carried out, then the uniform young seedlings were selected and transplanted. 2 strains per pot, at tillering stage (60-70 days), were treated according to the following scheme: (1) the selenium-doped nano-silica sol prepared according to example 1 (having a $SiO_2$ mass percentage of 20%, and a Se mass percentage of 1%) for foliar application was diluted 100-folds with deionized water, then carried out the foliar application, until the drops of water appeared on the foliage but did not dripped down (this treatment was noted as 1% Se—Si); (2) the silica sol prepared according to our previous invention patent (CN 101851133 B) (having a $SiO_2$ mass percentage of 20%) for foliar application was diluted 100-folds with deionized water, then carried out foliar application, until the drops of water appear on the foliage but did not dripped down (this treatment was noted as Si); (3) the solution formulated with a commercially available sodium selenite (having a Se mass percentage of 1%) for foliar application was diluted 100-fold with deionized water, then carried out foliar application, until the drops of water appeared on the foliage but did not dripped down (this treatment was noted as 1% Se); (4) the application of equivalent amount of deionized water was used as a control (noted as CK). Each of the treatments was repeated four times, and the rices were harvested after they were matured. The dry weight of rice per pot was weighed, and the arsenic and selenium contents in rice were analyzed.

Figure 3:
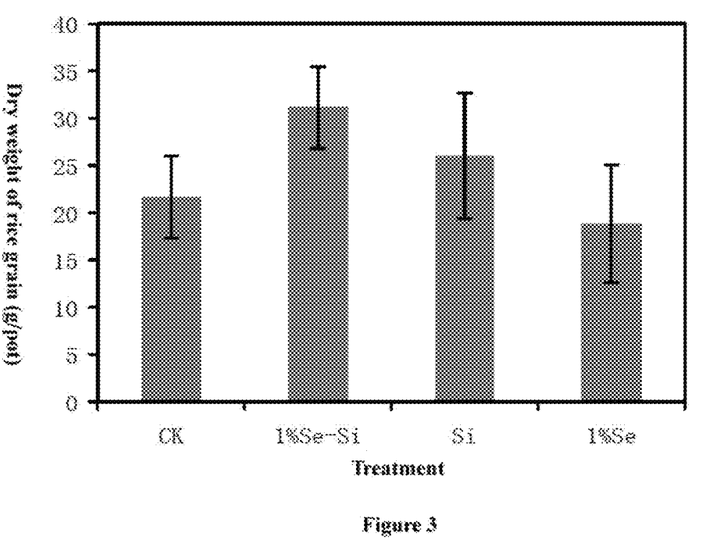
FIG. 3 shows the effects of the application of different fertilizers on the dry weight of rice grain in the pot experiments in example 4.
Figure 4:
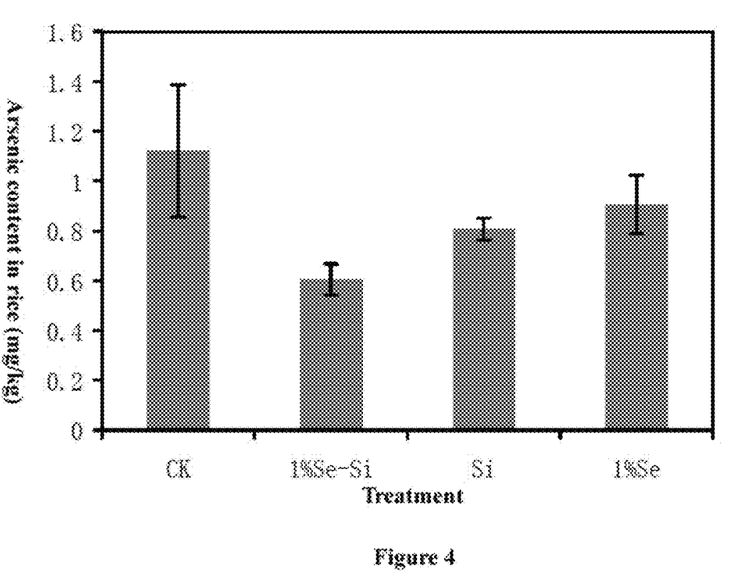
FIG. 4 shows the effects of the application of different fertilizers on the arsenic content in rice in the pot experiments in example 4.
Figure 5:
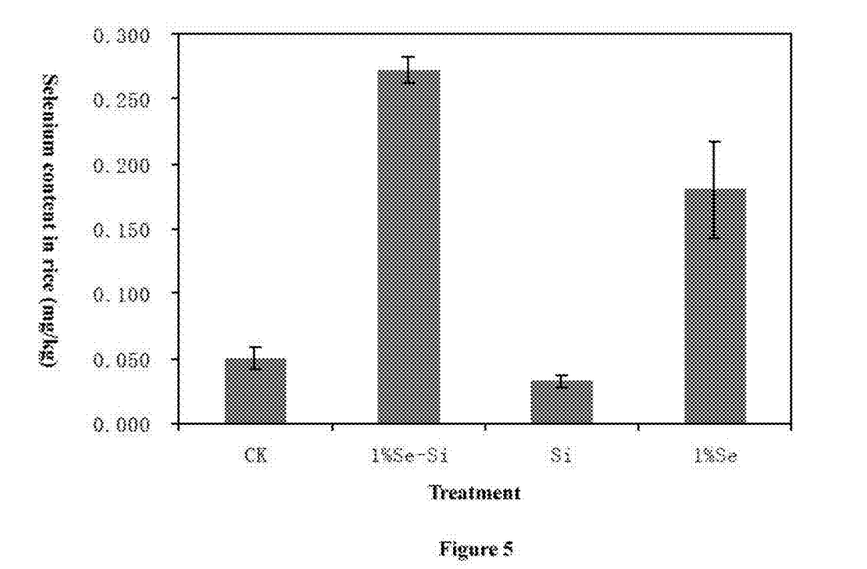
FIG. 5 shows the effects of the application of different fertilizers on the selenium content in rice in the pot experiments in example 4.

The results were shown in FIGS. 3, 4 and 5: the foliar application of the silica sol or the selenium-doped nano-silica sol with a selenium content of 1% in example 1 can significantly promote the growth of rice, the dry weights of the rice grain were increased by 20.2% and 43.8% respectively, as compared with the control; and as compared with the foliar application of the silica sol, the foliar application of the selenium-doped nano-silica sol with a selenium content of 1% had a more significant promotion effect on the growth of rice. However, the foliar application of an aqueous solution prepared with 1% sodium selenite had an inhibitory effect on the growth of rice; the dry weight of rice grain was reduced by 13.1% as compared with the control. The foliar application of the selenium-doped nano-silica sol can not only promote the growth of rice, but also can inhibit the accumulation of arsenic in rice, and increase the selenium content of rice. As compared with the control, the folia application of the selenium-doped nano-silica sol with a selenium content of 1% can reduce the arsenic content in rice by 46%; and the application of the pure silica sol can reduce the arsenic content in rice by 28%, and the application of an aqueous solution prepared with 1% sodium selenite can reduce the arsenic content in rice by 19%. The foliar application of the selenium-doped nano-silica sol with a selenium content of 1% can increase the selenium content in rice to 0.272 mg/kg from 0.050 mg/kg in the control; which met the selenium-rich rice standard. However, after the foliar application of an aqueous solution prepared with 1% sodium selenite, the selenium content in rice was 0.180 mg/kg; which was only 66% of that after the foliar application of the selenium-doped nano-silica sol with a selenium content of 1%. Therefore, the foliar application of the selenium-doped nano-silica sol produced according to the present patent on rice can further increase the effects of the foliage silicon fertilizer in inhibiting the absorption of arsenic in rice, and at the same time can produce a selenium-rich rice; and was more safe and efficient as compared with the direct application of sodium selenite solution.

Example 5

The field experiment for showing the effect of reducing the absorption of the heavy metal arsenic in rice by the foliar application of the selenium-doped nano-silica sol.

Experimental site: an arsenic-contaminated rice field in Yanhong Town, Chenghai District, Shantou City, Guangdong Province, China, and the basic physical and chemical properties of the soil were as follows: pH 6.12, total arsenic 93.6 mg/kg, total selenium 0.879 mg/kg. The rice variety was Peizashuangqi.

The method for the foliar application of the selenium-doped nano-silica sol in rice field was as follows:

(1) The application time: at rice tillering stage (about 60 days), about 4:00 in the afternoon in sunny or cloudy days was chosen to carry out the application; if it rained within 24 hours after the application, then a supplemental application was carried out once.

(2) The concentration and dosage of the application: a series of gradient concentration of the selenium-doped nano-silica sols produced in example 1 were used, wherein the silicon content was 20%, and the selenium contents were 0.1%, 0.5%, 1% and 2%, respectively; the usage amount was about 1 L per mu, they were blended with 100 L of water, then carried out the foliar application; the application of the equivalent amount of clear water was used as a control; which were noted as 0.1% Se—Si, 0.5% Se—Si, 1% Se—Si, 2% Se—Si, and CK, respectively. Each of them was used to treat four plots, and a random block arrangement was carried out.

(3) The field management: the same as the ordinary rice field management. After the rices were matured, they were harvested, and analyzed the cadmium and selenium contents in rice in each of the plots.

Figure 6:
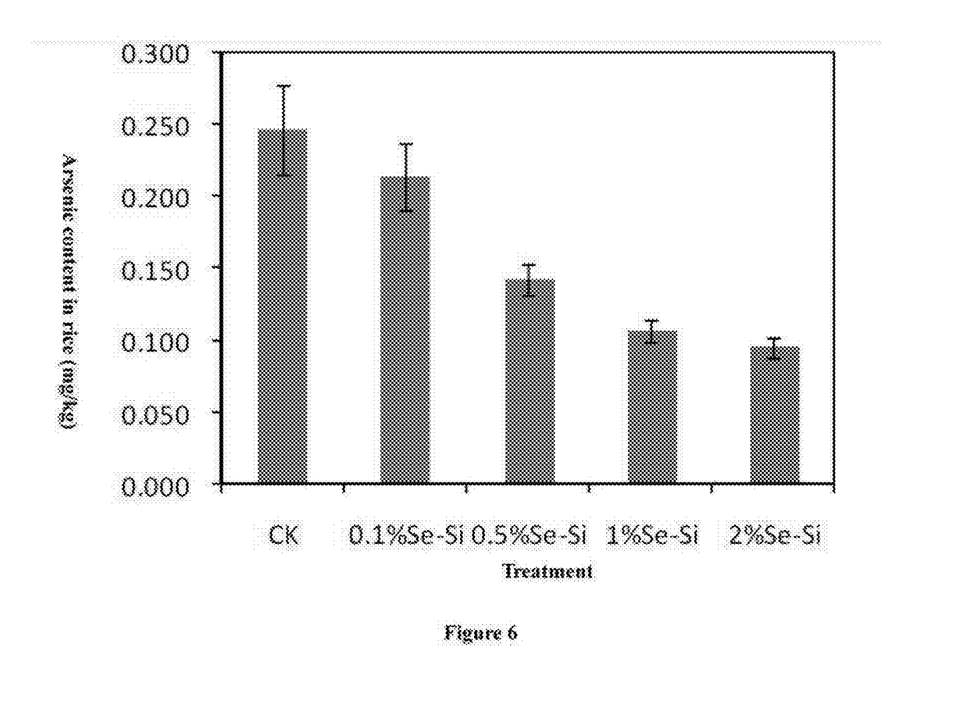
FIG. 6 shows the effects of the application of different concentrations of the selenium-doped silica sol on the arsenic content in rice in the arsenic contaminated farmland in Yanhong Town in example 5.
Figure 7:
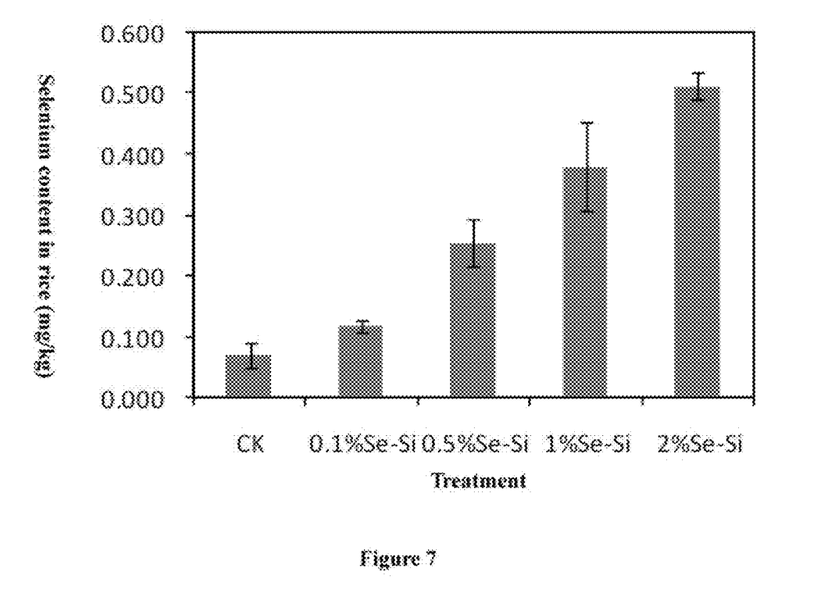
FIG. 7 shows the effects of the application of different concentrations of the selenium-doped silica sol on the selenium content in rice in the arsenic contaminated farmland in Yanhong Town in example 5.

The results were shown in FIGS. 6 and 7: the field experiments in Yanhong Town confirmed that the folia application of different concentrations of selenium-doped nano-silica sol can significantly inhibit the absorption and accumulation of arsenic in rice, and increase the selenium content in rice; and with the selenium doping amount increasing, the selenium content in rice was significantly increased, and the arsenic content in rice was significantly decreased. As compared with the control, the foliar application of 0.1%, 0.5%, 1% and 2% the selenium-doped nano-silica sol respectively, can reduce the arsenic content in rice by 19.1%, 45.9%, 59.4% and 63.7% respectively; and increase the selenium contents in rice by 67.5%, 265%, 443% and 631% respectively. When the selenium doping concentration reached 0.5%, the arsenic content in rice met the National Food Safety Standard (inorganic arsenic<0.2 mg/kg GB2762—2012); and when the selenium doping amounts were 0.1% and 0.5%, the selenium contents in rice were 0.12 mg/kg and 0.26 mg/kg respectively, which met the selenium-rich rice standard. Therefore, a selenium-rich rice with the arsenic content meeting the standard can be produced in the arsenic-contaminated farmland in Yanhong Town by the foliar application of the selenium-doped nano-silica sol with a selenium content of 0.5%.

Example 6

The field experiment for showing the effect of reducing the absorption of the heavy metals cadmium and arsenic in rice by the foliar application of the selenium-doped nano-silica sol.

Experimental site: a cadmium-contaminated farmland, in Zhangshi Town, Qujiang District, Shaoguan City, Guangdong Province, China, and the properties of the farmland soil were pH 5.32, total Cd content 0.905 mg/kg, and total selenium content 0.512 mg/kg. The rice variety was Meixiang.

The method for the foliar application of the selenium-doped nano-silica sol prepared in example 1 in rice field: the same as that in example 7.

Figure 8:
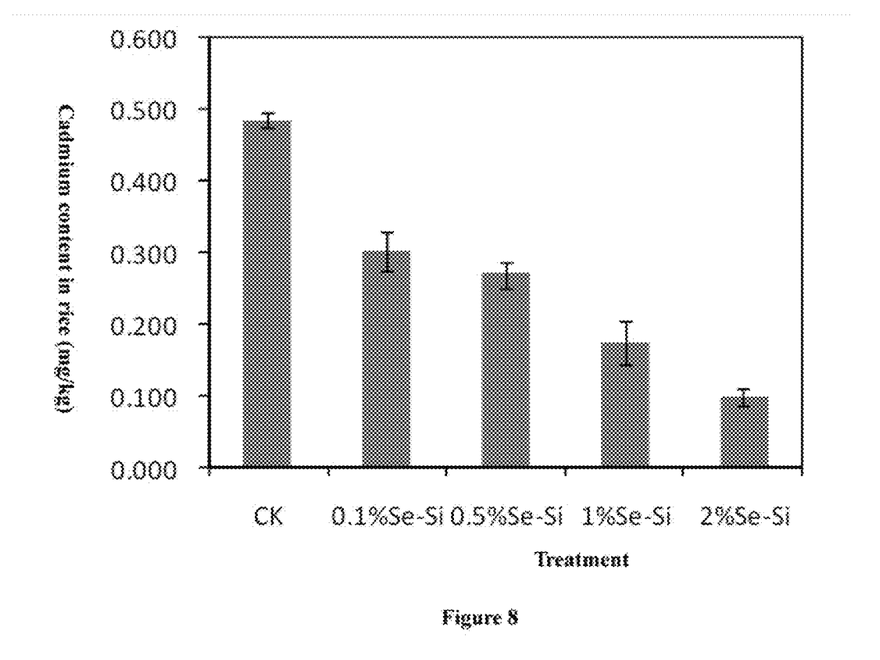
FIG. 8 shows the effects of the application of different concentrations the selenium-doped silica sol on the cadmium content in rice in the cadmium-contaminated farmland in Zhangshi Town in example 6.
Figure 9:
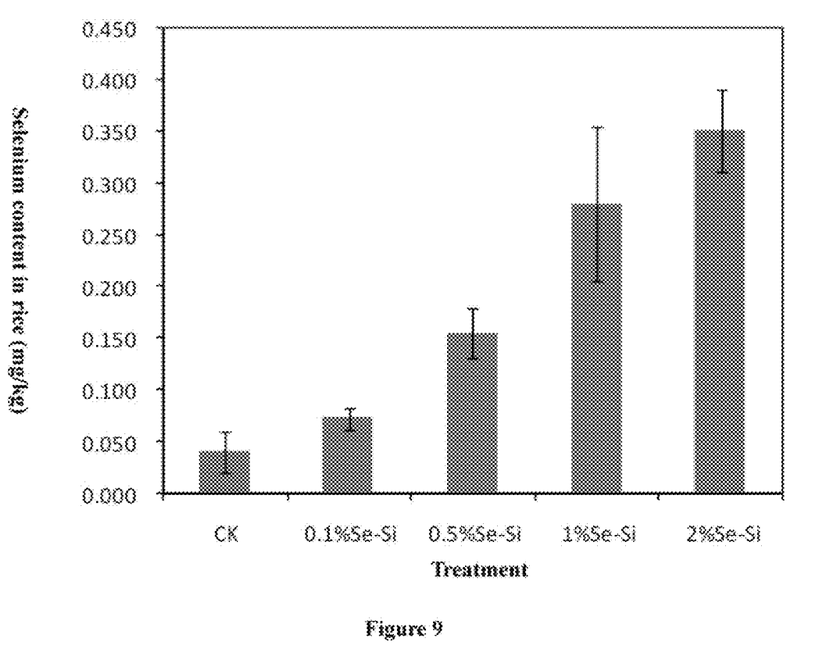
FIG. 9 shows the effects of the application of different concentrations of the selenium-doped silica sol on the selenium content in rice in the cadmium contaminated farmland in Zhangshi Town in example 6.

The results were shown in FIGS. 8 and 9: the field experiments in Zhangshi Town confirmed that the foliar application of different concentrations of the selenium-doped nano-silica sol can significantly inhibit the absorption and accumulation of cadmium in rice, and increase the selenium content in rice; and with the selenium doping amount increasing; the selenium content in rice was significantly increased, and the cadmium content in rice was significantly decreased. As compared with the control, the foliar application of 0.1%, 0.5%, 1%, and 2% of the selenium-doped nano-silica sol respectively can reduce the cadmium contents in rice by 37.5%, 44.4%, 63.9% and 79.6% respectively; and increase the selenium contents in rice by 80.7%, 288%, 600% and 778% respectively. When the selenium doping concentration reached 1%, the cadmium content in rice was decreased to 0.2 mg/kg or less, which met the National Food Safety Standard (cadmium<0.2 mg/kg GB 2762—2012); and when the selenium dopping amounts were 0.5% and 1%, the selenium contents in rice were 0.16 mg/kg and 0.28 mg/kg respectively; which met the selenium-rich rice standard. Therefore, a selenium-rich rice with the cadmium content meeting the standard can be produced in the cadmium-contaminated farmland in Zhangshi Town by the foliar application of the selenium-doped nano-silica sol with a selenium content of 1%.

The invention claimed is:

1. A method for preparing a selenium-doped nano-silica sol capable of both inhibiting the absorption and accumulation of heavy metal in rice and producing a selenium-rich rice, characterized by comprising the steps of:
   (1) preparation of a metal silicate solution, comprising: a metallic silicon powder or a metal silicate is added with stirring to an alkaline solution with a concentration of 0.1~5 M, so as to prepare a metal silicate solution, with a concentration of the metallic silicon powder or the metal silicate of 5% by weight to saturation, pH 10~13; wherein the metal silicate is $Na_2SiO_3$, $K_2SiO_3$ or $Li_2SiO_3$;
   (2) preparation of an acidic silica sol precursor, comprising: the metal silicate solution is subjected to a cation exchange treatment, the collected solution is controlled at a pH of 1~4, the collected solution is heated to 35-90° C., then carried out standing, cooling, and aging, so as to obtain an acidic silica sol precursor;
   (3) preparation of an acidic selenium-doped solution, comprising: a selenium-containing compound is dissolved in a dilute acid solution with stirring, so as to prepare an acidic selenium-doped solution with a selenium content of 0.1~10% by mass, and the acidic selenium-doped solution is controlled at a pH of 1~4; wherein the selenium-containing compound is selenious acid, sodium selenite, potassium selenite or sodium hydrogen selenite;
   (4) preparation of a selenium-doped emulsion, comprising: an emulsifier is added with stirring to the acidic selenium-doped solution in step (3), the final mass percentage of the emulsifier is controlled at 0.05~5%, so as to obtain a selenium-doped emulsion; wherein the emulsifier is polyvinylpyrrolidone, or polyvinyl alcohol;
   (5) preparation of a selenium-doped acidic silica sol precursor, comprising: the selenium-doped emulsion in step (4) is added with stirring to the acidic silica sol precursor in step (2), so as to obtain a selenium-doped acidic silica sol precursor, wherein the selenium-doped acidic silica sol precursor has a mass percentage ratio between silicon and selenium of 3~200:1;
   (6) the selenium-doped acidic silica sol precursor in step (5) is added to an alkaline solution formulated with a basic catalyst at 30° C.–90° C., the addition is not stopped until the alkaline solution arrives at a pH value of 7~9, stirring and reaction are continued for 30~90 min, so as to obtain a selenium-doped silica sol precursor; wherein the basic catalyst is sodium hydroxide, potassium hydroxide, urea, aqueous ammonia, or sodium silicate solution;
   (7) the selenium-doped silica sol precursor in step (6) is added to a reducing agent solution at 30° C.–90° C., until the pale red color of the sol is no longer deepened, after selenium is sufficiently reduced, the sol is continued to stir and react for 2 hours or more time, and then dialyzed twice or more times, so as to obtain a selenium-doped nano-silica sol; wherein the reducing agent is ascorbic acid, glutathione, or reducing sugars.

2. A method according to claim 1, characterized in that the alkaline solution in step (1) is formulated with sodium hydroxide, potassium hydroxide or aqueous ammonia, with a concentration of 0.1~2 M.

3. A method according to claim 1, characterized in that the collected solution in step (2) has a PH of 2~3.5, and the collected solution is heated to a temperature of 45-55° C.

4. A method according to claim 1, characterized in that the dilute acid solution in step (3) is dilute hydrochloric acid, dilute nitric acid, dilute sulfuric acid or dilute phosphoric acid solution; the selenium content in the acidic selenium-doped solution is 2~7.6% by mass;
and the acidic selenium-doped solution is controlled at a PH of 1~2.

5. A method according to claim 1, characterized in that the emulsifier in step (4) is Tween, and the final mass percentage of the emulsifier is controlled at 0.5~2%.

6. A method according to claim 1, characterized in that the selenium-doped acidic silica sol precursor in step (5) has a mass percentage ratio between silicon and selenium of 9~20:1.

7. A method according to claim 1, characterized in that the alkaline solution formulated with a basic catalyst in step (6) is controlled at a temperature of 45° C.~85° C., and the stirring and reaction is continued for 30~60 min.

8. A method according to claim 1, characterized in that the reducing agent in step (7) is ascorbic acid, and the solution is controlled at a temperature of 50° C.~85° C.

* * * * *